United States Patent [19]
Takaishi et al.

[11] Patent Number: 5,041,786
[45] Date of Patent: Aug. 20, 1991

[54] METHOD OF NONDESTRUCTIVELY INSPECTING FOR FLAWS IN METAL STOCKS INCLUDING SELECTION OF DETECTION COIL DIAMETER.

[75] Inventors: Kazuhide Takaishi, Yamaguchi; Akira Saeki, Tokyo; Toshiki Kadonaga; Noritsugu Fujii, both of Yamaguchi, all of Japan

[73] Assignees: Kobe Steel, Ltd., Kobe; Eddio Corporation, Tokyo, both of Japan

[21] Appl. No.: 395,753

[22] Filed: Aug. 18, 1989

[30] Foreign Application Priority Data

Aug. 19, 1988 [JP] Japan .................... 63-204768

[51] Int. Cl.$^5$ ............ G01N 27/90; G01R 33/12
[52] U.S. Cl. .................... 324/240; 324/237; 324/238
[58] Field of Search ............ 324/224-243

[56] References Cited

U.S. PATENT DOCUMENTS

| 3,588,682 | 6/1971 | Forster | 324/227 X |
| 3,906,357 | 9/1975 | Runshang | 324/227 X |
| 3,964,740 | 9/1972 | Bergstrand | 324/240 X |
| 4,507,610 | 3/1985 | Nakaoka | 324/240 X |
| 4,534,405 | 8/1985 | Hulek et al. | 324/240 X |
| 4,628,261 | 12/1986 | Hüschelrath et al. | 324/240 |
| 4,641,092 | 2/1987 | Sakamoto et al. | 324/240 X |

Primary Examiner—Kenneth Wieder
Assistant Examiner—Warren S. Edmonds
Attorney, Agent, or Firm—Flynn, Thiel, Boutell & Tanis

[57] ABSTRACT

A method of nondestructively inspecting a magnetic substance such as metal pipe and bar stocks, wherein the method provides a detection coil having a diameter which is specified based on the length of existent peripheral surface flaws such that the directional sensitivity of the detection coil relative to those flaws is improved. The magnetic substance is moved along an axis thereof and has an eddy current induced therein. Relative rotation of the detection coil around the magnetic substance is effected to permit detection of surface flaws.

12 Claims, 4 Drawing Sheets

METHOD OF NONDESTRUCTIVELY INSPECTING FOR FLAWS IN METAL STOCKS INCLUDING SELECTION OF DETECTION COIL DIAMETER.

BACKGROUND OF THE INVENTION

1. Field of the Invention

The present invention relates to nondestructive inspection of metal stocks, and more specifically to a method of nondestructively inspecting metal pipe and bar stocks by an eddy current to detect a physical and/or metallurgical anomaly such as a flaw produced in the metal pipe and bar stocks.

2. Description of the Prior Art

Referring to FIG. 5, a prior nondestructive flaw inspection apparatus is illustratively shown in a cross sectional view, wherein an alternating magnetic field is applied to a sample to be inspected such as a metal pipe or a metal bar, etc., and a change in an eddy current produced in the sample is detected as any flaw being existent in the sample.

As shown in the figure, a sample 1 to be inspected such as a metal pipe or bar is transferred along its axis to the right at a low speed, and allowed to traverse the vicinity of a sensor 3 provided with an excitation/detection coil 2. The excitation/detection coil 2 is supplied with a radio frequency (RF) current from a RF power supply 6 and is allowed to generate a RF magnetic field on the sample 1 at a proper angle. This induces an eddy current along the sample 1. The sensor 3 is rotated by a rotary mechanism 4 around the sample 1 at a relatively high rotational speed together with the excitation/detection coil 2 to detect any change in the aforementioned eddy current flowing through the surface area of the sample 1, the change being caused by the existence of any flaw in the surface area of the sample 1. The change in the eddy current detected by the sensor 3 is fed to a signal processor 7.

Referring here to FIG. 6, orientations of surface flaws, which are assumed to be produced in the surface area of the sample 1, are depicted illustratively. In the prior nondestructive flaw inspection apparatus, the sensor 3 detects with ease a surface flaw L, which is oriented axially of the sample 1, because the sensor 3 scans the sample surface in a direction perpendicular to the surface flaw L, but it is difficult to detect a surface flaws when it is oriented as shown, particularly when it is short in length.

To solve the difficulty, U.S. Pat. No. 4,439,730 discloses a nondestructive inspection technique with use of a Hall element as a sensor, wherein two orthogonal steady magnetic fields are passed through an object to be inspected such as a pipe wall region, and a resulting composite signal from the object is detected and displayed. Hereby, the oriented flaw existing near a surface area of the object might be detected. However, the Hall element as a sensor is impracticable to the present situation where the excitation/detection coil is employed as a sensor to detect an eddy current produced in a sample.

SUMMARY OF THE INVENTION

In view of the drawbacks of the prior techniques, it is an object of the present invention to provide a method of nondestructively inspecting a magnetic substance by an eddy current, the method being capable of detecting a non-axially oriented flaw existing in the vicinity of a peripheral surface area of the metal pipe stock or the metal bar stock with high reliability compared with the prior techniques by providing a detection coil of a diameter which is specified in due consideration of the length of the non-axially oriented flaw.

To achieve the above object, a method of nondestructively inspecting a magnetic substance by an eddy current induced in the same comprises the steps of: (a) moving the magnetic substance to be inspected along its axis and passing the same through an excitation coil; (b) applying an excitation alternating magnetic field to said magnetic substance to be inspected through said excitation coil which is supplied with an excitation alternating current from a power supply; (c) rotating the excitation coil at a proper rotational speed to sweep the peripheral surface area of the magnetic substance with the excitation alternating magnetic field keeping a predetermined distance from the peripheral surface of the magnetic substance; (d) detecting through a detection coil a change in a magnetic field which is produced by an eddy current, the eddy current being induced by said excitation alternating magnetic field applied by said excitation coil to the magnetic substance, said change being caused by the existence of any flaw in the peripheral surface area of the magnetic substance owing to the disturbance of the eddy current by said flaw; and (e) specifying the diameter of said detection coil such that the directional characteristic of sensitivity of said detection coil to the flaw is substantially independent from the flaw existent in the peripheral surface area of said magnetic substance with respect to the mean distance of those flaws.

In accordance with the present invention, the directional characteristic of sensitivity of the detection coil to any flaw can greatly be moderated so that any flaw existing in the peripheral surface area of a magnetic substance, if non-axially oriented, is detected substantially with the same sensitivity as that for a flaw existing in the same area but oriented axially of the substance.

The above and other objects, features and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIGS. 1(a) through 3(b) are views illustrating waveforms indicative of the existences of flaws in the peripheral surface areas of magnetic substances to be inspected, which are detected by embodying a method according to the present invention;

DESCRIPTION OF THE PREFERRED EMBODIMENT

In the following, a preferred embodiment of a method of nondestructively inspecting metal stocks by eddy current according to the present invention will be described with reference to the accompanying drawings.

Figure 4:
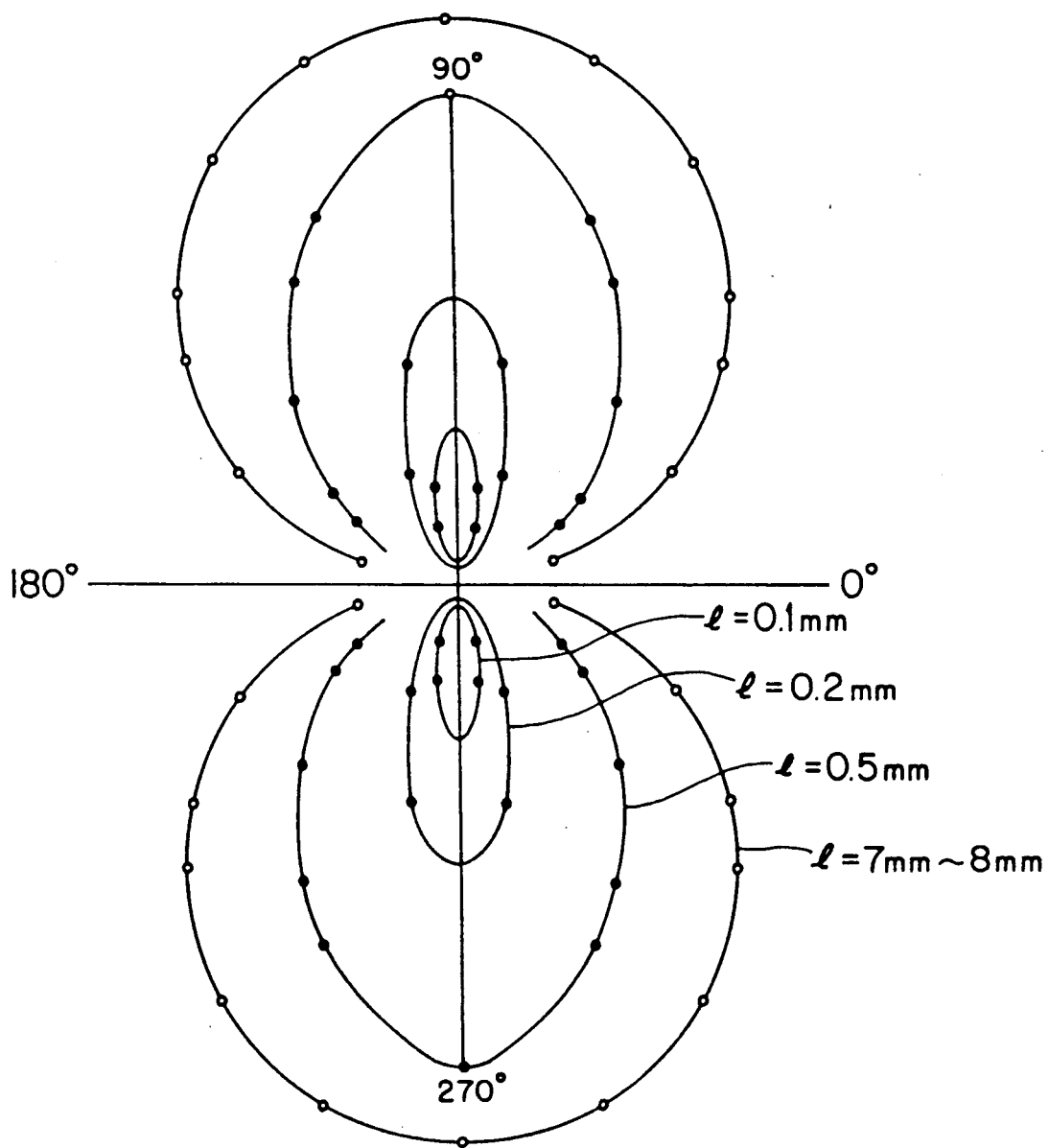
FIG. 4 is a view illustrating a relation between directional characteristic of sensitivity of a detection coil of the present invention and the lengths of flaws.
Figure 5:
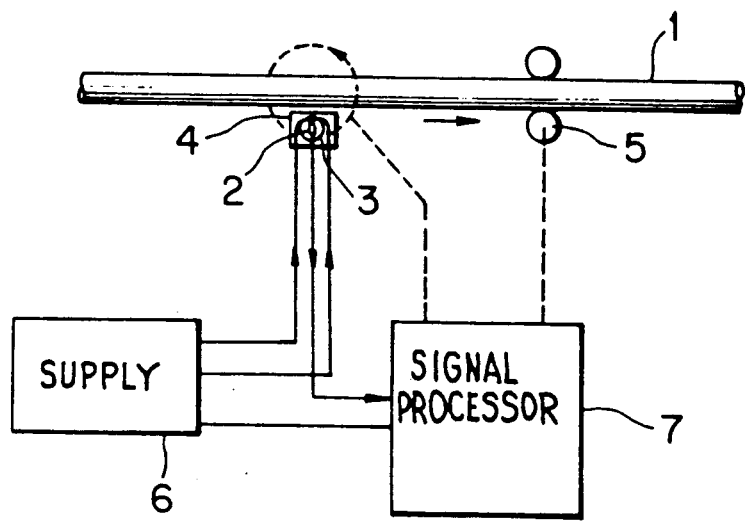
FIG. 5 is a block diagram illustrating a main portion of the general arrangement of a nondestructive flaw inspection apparatus by an eddy current.
Figure 6:
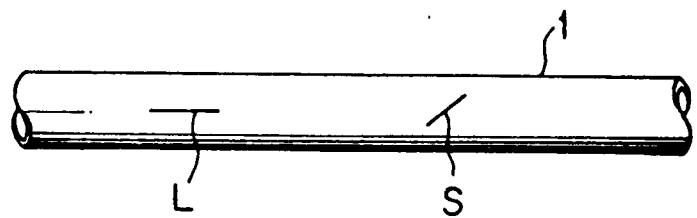
FIG. 6 is a view illustrating the orientations of flaws existing in the peripheral surface area of a magnetic substance.

A nondestructive flaw inspection apparatus embodying the present method is substantially the same as that described in the prior art and illustrated in FIG. 5, but in the present embodiment the excitation/detection coil, which was employed in the prior art, is specially designed to manifest the feature of the present invention such that the directional characteristic of sensitivity thereof to a surface flaw is substantially independent from the flaw existent in the peripheral area of the magnetic substance such as a metal pipe stock and a metal bar stock with respect to the mean length of those flaws. The feature is based upon an experimental finding by the present inventors that when varieties of lengths l of surface flaws are measured with use of a sensor equipped with a coil, i.e., an excitation/detection coil in the present embodiment, of a predetermined diameter R to elucidate directional characteristic of sensitivity of the coil, for surface flaws of reduced lengths l, a directional pattern of sensitivity of the coil is more sharpened, but it is rounded exhibiting an ellipsoidal shape as the angle $\theta$ of the surface flaw with respect to the direction of scanning of the coil goes out of 90°, while for surface flaws of increased length l the directional pattern is more rounded exhibiting a circular shape, as illustrated in FIG. 4.

In what follows, further detail of the present method will be described with a concrete example.

The just-mentioned flaw inspection apparatus, which incorporates therein the just-mentioned excitation/detection coil, is employed to measure the existence of any flaw in the peripheral area of a magnetic substance, i.e., Zircaloy pipe under the conditions listed in Table 1 below.

TABLE 1

| Magnetic Substance to be inspected | Zircaloy pipe, a liner coated pipe for nuclear fuel (12,523 $\phi$ × 0.86 t) |
| --- | --- |
| Scanning method | Rotating sensor |
| Sensor coil diameter | 1.0 mm |
| Flaw inspection system | Single frequency |
| Frequency used | 500 KHz-3 MHz |
| Distance between the sensor and the substance | 0.1-0.2 mm |

(here, $\phi$ denotes inch, and t thickness)

Figure 1:
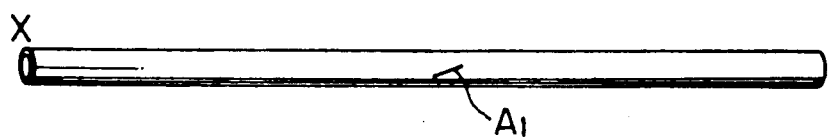
Figure 1:
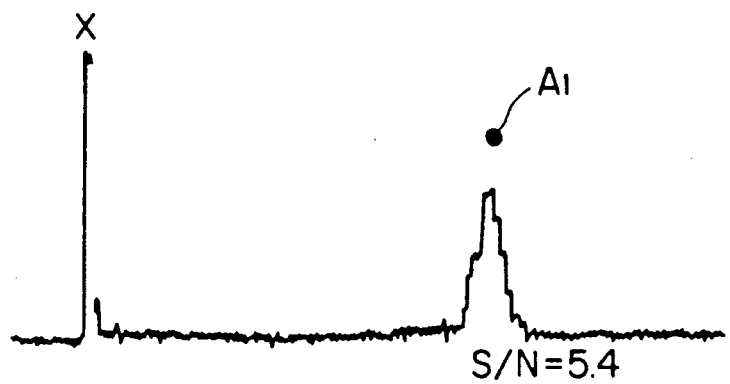
Figure 2:
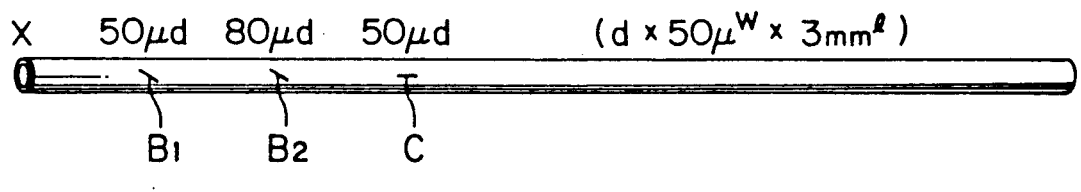
Figure 2:
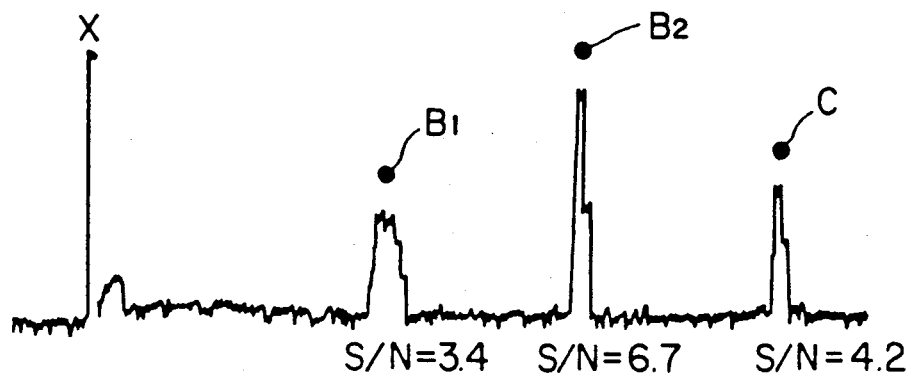
Figure 3A:
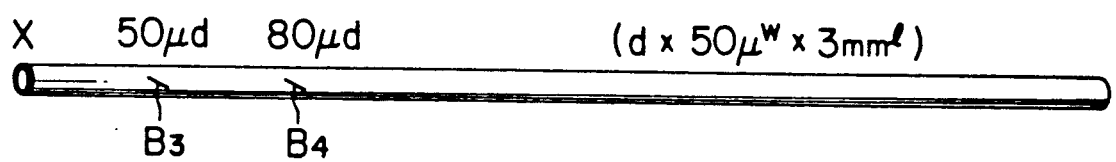
Figure 3B:
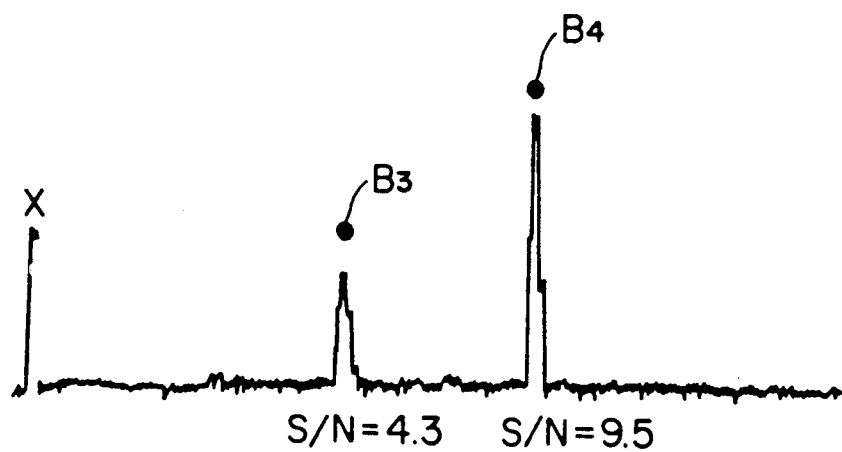

FIG. 1(a) illustrates a non-axially oriented rolling crack $A_1$ produced in the peripheral surface area of the Zircaloy pipe, and FIG. 1(b) illustrates a waveform of the rolling crack $A_1$ of FIG. 1(a) detected by the present apparatus, wherein X denotes a pipe end and the abscissa corresponds to a location on the bar of FIG. 1(a) relative to the pipe end. Likewise, FIGS. 2(b) and 3(b) illustrate detected waveforms of artificial flaws illustrated correspondingly in FIGS. 2(a) and 3(a) as designated at $B_1$ and $B_2$ for 45° oriented flaws and C for a 90° flaw in the former figure, and $B_3$ and $B_4$ for 45° oriented flaws in the latter figure. Here, in the respective figures, l is the length (mm) of the flaw, d the depth ($\mu$m) of the flaw, and w the width ($\mu$m) of the same.

It is clearly shown from the example described above that the excitation/detection coil of 1.0 mm diameter can securely detect the 45° oriented flaw of 3 mm length with a high S/N ratio. The present inventors have found experimentally that the diameter R of the excitation/detection coil may be about $\frac{1}{3}$ of the average length $l_{MEAN}$ of flaw lengths for detection of a 45° oriented flaw. Thus, the method of the present invention can securely detect a smaller oriented flaw of an angle with respect to the direction of scanning of the sensor by employing the sensor having a directional characteristic being an approximately circular pattern for a surface flaw of length l.

To detect a rolling flaw produced in a Zircaloy pipe, there is hitherto known an ultrasonic flaw detection method, which is however difficult to detect a non-axially oriented flaw in a Zircaloy pipe. However, a combination of the present invention, which assures the detection of such a flaw as described above, and the just-mentioned ultrasonic flaw detection method could detect such a surface flaw without missing the same, and, as a result improve the safety of a nuclear reactor, manifesting greater practical applicability of the present invention.

It should be noted here that the number of the detection coils and the rotational speed of the same are specified taking the diameter and feed rate of a sample to be inspected, and the frequency of occurence of surface flaws, etc., into consideration, and radio frequency voltage to be applied to the detection coil and the frequency of the voltage, etc., are also determined into optimum ones based upon the material quality of the sample and the shape of a flaw.

Although in the preferred embodiment described above the sensor was rotated, it may be fixedly mounted and instead a sample to be inspected may be rotated.

In accordance with the present invention, as described above, the diameter of the detection coil was determined on the basis of the length of an existent flaw to establish substantially non-directional sensitivity of detection of the flaw. This assures that any surface flaw, even if short and non-axially oriented, one, can be detected with the sensitivity of detection substantially equal to that for an axial flaw in a pipe or bar stock, sharply improving the flexibility and reliability of the flaw inspection by an eddy current.

Although a certain preferred embodiment has been shown and described, it should be understood that many changes and modification may be made therein without departing from the scope of the appended claims.

What is claimed is:

1. A method for nondestructively inspecting for flaws in an outer peripheral surface of a magnetic substance, utilizing an eddy current induced in the magnetic substance, the method comprising the steps of:

defining a class of targeted flaws to be all flaws in the outer peripheral surface of the magnetic substance which have a predetermined minimum linear dimension;

providing a detection coil having a diameter which is less than said predetermined minimum linear dimension associated with said targeted flaws;

moving the magnetic substance to be inspected along an axis and passing the magnetic substance adjacent an excitation coil;

inducing an eddy current in the magnetic substance, including applying an excitation alternating magnetic field to said magnetic substance through said excitation coil by supplying said excitation coil with an excitation alternating current from a power supply;

rotating the excitation coil at a proper rotational speed to sweep the outer peripheral surface area of the magnetic substance with the excitation alternating magnetic field, while keeping said excitation coil spaced a predetermined distance from the peripheral surface of the magnetic substance;

effecting relative rotation of the detection coil around the magnetic substance to sweep the outer peripheral surface area of the magnetic substance; and detecting through said detection coil whether a change occurs in a magnetic field produced by said eddy current, said change being caused by a disturbance in the eddy current due to the presence of a targeted flaw in the outer peripheral surface of the magnetic substance.

2. A method according to claim 1, wherein the diameter of said detection coil is ⅓ or less of the predetermined minimum linear dimension of the targeted flaws existent in the peripheral surface of the magnetic substance.

3. A method according to claim 1, wherein said magnetic substance includes a metal pipe stock or a metal bar stock.

4. A method according to claim 1, wherein said detection coil has a substantially circular directional pattern of sensitivity.

5. A method according to claim 1, wherein at least one of said targeted flaws in the peripheral surface of the magnetic substance is oriented transversely with respect to the axis of the magnetic substance.

6. A method according to claim 1, wherein at least one said targeted flaws forms with said axis an angle of less than 45°.

7. A method according to claim 1, wherein said magnetic substance is a Zircaloy pipe.

8. A method according to claim 1, wherein said detection coil is held stationary, the magnetic substance being rotated.

9. A method according to claim 2, wherein said magnetic substance includes a metal pipe stock or a metal bar stock.

10. A method according to claim 5, wherein at least one of said targeted flaws forms with said axis an angle of less than 45°.

11. A method according to claim 3, wherein said magnetic substance is a Zircaloy pipe.

12. A method for nondestructively inspecting for flaws in an outer peripheral surface of a metal stock, comprising the steps of:

defining a class of targeted flaws to be all flaws in the outer peripheral surface of the metal stock which have a predetermined minimum linear dimension;

providing a detection coil having a diameter which is less than said predetermined minimum linear dimension associated with said targeted flaws;

inducing an eddy current in the metal stock; and effecting relative motion between said detection coil and the metal stock such that said detection coil is rotated around the outer peripheral surface of the metal stock while simultaneously passing along a length of the metal stock.

* * * * *